(12) United States Patent
Bjorling

(10) Patent No.: US 8,577,449 B2
(45) Date of Patent: Nov. 5, 2013

(54) METHOD AND SYSTEM FOR ISCHEMIA DETECTION

(75) Inventor: Anders Bjorling, Solna (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/528,695

(22) Filed: Jun. 20, 2012

(65) Prior Publication Data

US 2013/0023779 A1 Jan. 24, 2013

Related U.S. Application Data

(60) Provisional application No. 61/502,518, filed on Jun. 29, 2011.

(30) Foreign Application Priority Data

Jun. 20, 2011 (EP) .................................... 11170536

(51) Int. Cl.
*A61B 5/0456* (2006.01)
(52) U.S. Cl.
USPC ........................................................ 600/521
(58) Field of Classification Search
None
See application file for complete search history.

(56) References Cited

U.S. PATENT DOCUMENTS 7,865,232 B1 * 1/2011 Krishnaswamy et al. .... 600/509

* cited by examiner

*Primary Examiner* — Carl H Layno
*Assistant Examiner* — Paula J Stice

(57) ABSTRACT

Disclosed are systems and methods for automatically determining ST windows for ischemia detection. An IEGM signal is obtained over a period of time a derivative signal of the IEGM signal is calculated. The R-wave is identified in the derivative signal and the derivative signal data following the identified R-wave is analyzed to find portions of the derivative signal comprising samples having lower values than a predetermined threshold. Further, a portion of the derivative signal including samples having lower values than the threshold is determined to correspond to a ST window for that cardiac cycle if that portion fulfills predetermined requirements. A reference ST window based on a number of determined ST windows is determined. Using the reference ST window, ischemia can be detected by comparing IEGM data in the reference ST window with current IEGM data from a segment of the IEGM signal corresponding to the reference ST window.

16 Claims, 4 Drawing Sheets

METHOD AND SYSTEM FOR ISCHEMIA DETECTION

CROSS REFERENCE TO RELATED APPLICATIONS

This application claims the benefit of U.S. Provisional Application Ser. No. 61/502,518, filed Jun. 29, 2011, entitled Method And System For Ischemia Detection, and European Patent Application EP 11170536.4, filed Jun. 20, 2011.

FIELD OF THE INVENTION

The present invention relates generally to implantable medical devices and more particularly to systems and methods for automatically determining ST windows for ischemia detection.

BACKGROUND OF THE INVENTION

Many patients at risk of cardiac ischemia have pacemakers, ICDs or other medical devices implanted therein. Cardiac ischemia is a severe condition and great efforts has therefore been made within the medical community to find systems and methods for detecting and monitoring ischemia over time. Electrocardiograms (ECG) are useful for diagnosing ischemia and locate damaged areas within the heart. Cardiac ischemia is a condition whereby heart tissue does not receive adequate amounts of oxygen and is usually caused by a blockage of an artery leading to damage of heart tissue. ECGs are composed of various waves and segments that represent the heart depolarization and repolarization. The ST segment represent the portion of the cardiac signal between ventricular depolarization and ventricular repolarization.

In the prior art, there exist techniques for detecting cardiac ischemia using implanted medical devices. In some conventional IEGM-based ischemia detection techniques, changes in the elevation or depression of the ST segment from a IEGM baseline are used an indication of ischemia. Elevation or depression of the ST segment in an IEGM signal may be the result of abnormalities in the polarization of cardiac tissue during an acute myocardial infraction (MI). An ST segment shift arises because the differences in the electric potential between cells that have become ischemic and those cells are still receiving normal blood flow. Deviation of an ST segment from a baseline is a result of an injury to the cardiac muscle, changes in the synchronization of ventricular muscle depolarization, drug or electrolyte influences, or the like.

In some prior art methods for determining ST window for ischemia detection, the ST window is a fixed time interval relative the R-wave. This may lead to that the ST window may encompass parts of the T-wave or the R-wave. If changes occur to the amplitude of the T-wave or R-wave, this may result in a false indication of an ST episode. Accordingly, there is a need of improving the specificity of these prior art methods. Such improvement can be achieved by allowing manual adjustments of the default parameters defining e.g. the fixed time interval to adapt the parameters to a specific patient.

In U.S. Pat. No. 7,865,232 to Krishnaswamy et al., a method and system for automatically determining ischemia detection parameters is disclosed. An ischemia detection window is based on physiological state indicators that define start and end of the ischemia detection window. The physiological state indicators can be located by identifying slope changes after the R-wave and before the T-wave, respectively. Slope changes are recognized by identifying when the derivative of the composite intrinsic baseline changes sign from positive to negative or vice versa following the R-wave marker. The slope changes are used to locate ischemia detection parameters (e.g. start and end of ST window). A first ischemia detection parameter (indicating the start of the ST window) can be identified as a point along the baseline following the first slope change but with a predetermined offset (e.g. about 25 msec). A second ischemia detection parameter (indicating the end of the ST window) can be identified as a point along the baseline preceding the third slope change with a negative offset (e.g. about 35 msec).

However, there is still a need within the art for a patient-specific determination of ST windows or segments for use in ischemia detection in order to inter alia improve the specificity of the ischemia detection.

SUMMARY OF THE INVENTION

According to an aspect of the present invention there is provided a method for ischemia detection comprising obtaining at least one IEGM signal representative of cardiac behavior of a patient over a period of time and calculating a derivative signal of the IEGM signal. The R-wave is identified in the derivative signal or in the original IEGM signal and data of the derivative signal following the identified R-wave is analyzed so as to find portions of the derivative signal comprising samples having lower values than a predetermined threshold. Further, a portion of the derivative signal including samples having lower values than the threshold is determined to correspond to a ST window for that cardiac cycle if that portion fulfills predetermined requirements. A reference ST window based on a number of determined ST windows is determined. Using the reference ST window, ischemia can be detected by comparing IEGM data in the reference ST window with current IEGM data from a segment of the IEGM signal corresponding to the reference ST window. A shift in the ST segment, i.e. the portion of the signal in the ST window, from a baseline or reference level is an indication of cardiac ischemia. For example, a depression of the IEGM signal in the ST window may be an indication of cardiac ischemia. Deviation of the ST segment from a baseline may be a result of an injury to cardiac muscle arising from differences in electric potential between cells that have become ischemic and those cells still receiving normal blood flow.

According to a second aspect of the present invention, there is provided a system for ischemia detection comprising a data collection module configured to obtain at least one IEGM signal indicating cardiac behavior of a cardiac cycle corresponding a heartbeat and a data processing module configured to calculate a derivative signal of the IEGM signal. Furthermore, the system comprises a morphology detector configured to identify an R-wave in the derivative signal or in the original IEGM signal and an ST window determining module. The ST window determining module is configured to analyze the derivative signal data following the identified R-wave so as to find portions of the derivative signal comprising samples having lower values than a predetermined threshold, determine a portion of the derivative signal including samples having lower values than the threshold to correspond to a ST window for that cardiac cycle if that portion fulfills predetermined requirements and create a reference ST window based on a number of determined ST windows. An ischemia detection module is configured to detect ischemia by comparing IEGM data in the reference ST window with current IEGM data from a segment of the IEGM signal corresponding to the reference ST window.

In preferred embodiments of the present invention, all or some modules of the system are implemented in an implantable medical device or cardiac stimulator such as a cardiac pacemaker (a dual or single chamber stimulation device), an implantable cardioverter defibrillator ("ICD"), a defibrillator, or an ICD coupled with a pacemaker.

In a further embodiment some modules are implemented in an extracorporal device such as a programmer. The collected IEGM signals may be stored in a memory. Examples of modules that may be located in a programmer that analyzes stored IEGM data that may be read out from a memory are the ST window determining module or the ischemia detection module. The division of modules for implementing the system may be made in several different ways.

According to embodiments of the present invention, the threshold is determined based on derivative signal data following the identified R-wave, such that the threshold is higher in a region following the R-wave. By making the threshold higher near the R-wave, the risk that a start point of an ST window is set to be too far away from the R-wave and/or too close to the T-wave can be significantly reduced. Preferably, the threshold is set to be linearly decreasing from the R-wave, for example, the peak value of the R-wave. Other shapes of the decreasing threshold can also be used, for example, quadratic, exponential, logarithmic, or step-wise. According to an embodiment of the present invention, the threshold has a value at a starting point of a search window being a multiple of the value of the threshold base sample and a value at an end point of the search window being lower than the value of the threshold base sample, wherein the threshold is linearly decreasing between the value of the starting point and the end point.

According to embodiments of the present invention, the predetermined requirements for determining a portion of the derivative signal to be a ST window comprises that:
 a predetermined number of samples in the portion has a value below the predetermined threshold;
 a predetermined number of samples having values below the threshold are consecutive; and
 the portion has a length exceeding a predetermined time interval.

According to embodiments of the present invention, the requirements for determining a portion of the derivative signal to be a ST window further comprises, if more than one portion fulfill the predetermined requirements to correspond to a ST window for that cardiac cycle, selecting the portion being closest to the R-wave to correspond to the ST window for that cardiac cycle.

According to embodiments of the present invention, an overall ST window is created by: identifying a predetermined number of ST windows, determining a starting point of the reference ST window based on starting points for the gathered ST windows, and determining an end point of the reference ST window based on end points for the gathered ST windows.

According to embodiments of the present invention, the sensitivity of the threshold is adjusted if a predetermined number of ST windows has not been identified during a predetermined period of time or from of a predetermined number of cardiac cycles. Thereafter, the derivative signal data following the identified R-wave is analyzed for each cardiac cycle so as to find portions of the derivative signal comprising samples having lower values than the adjusted threshold and a portion of the derivative signal including samples having lower values than the adjusted threshold is determined to correspond to an ST window for that cardiac cycle if that portion fulfills predetermined requirements.

These and other features, aspects and advantages of the invention will be more fully understood when considered with respect to the following detailed description, appended claims and accompanying drawings.

BRIEF DESCRIPTION OF THE DRAWINGS

The drawings are not necessarily drawn to scale and illustrate generally, by way of example, but no way of limitation, various embodiments of the present invention. Thus, exemplifying embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention. For example, embodiments may be used with a pacemaker, a cardioverter, a defibrillator, and the like.

Figure 1:
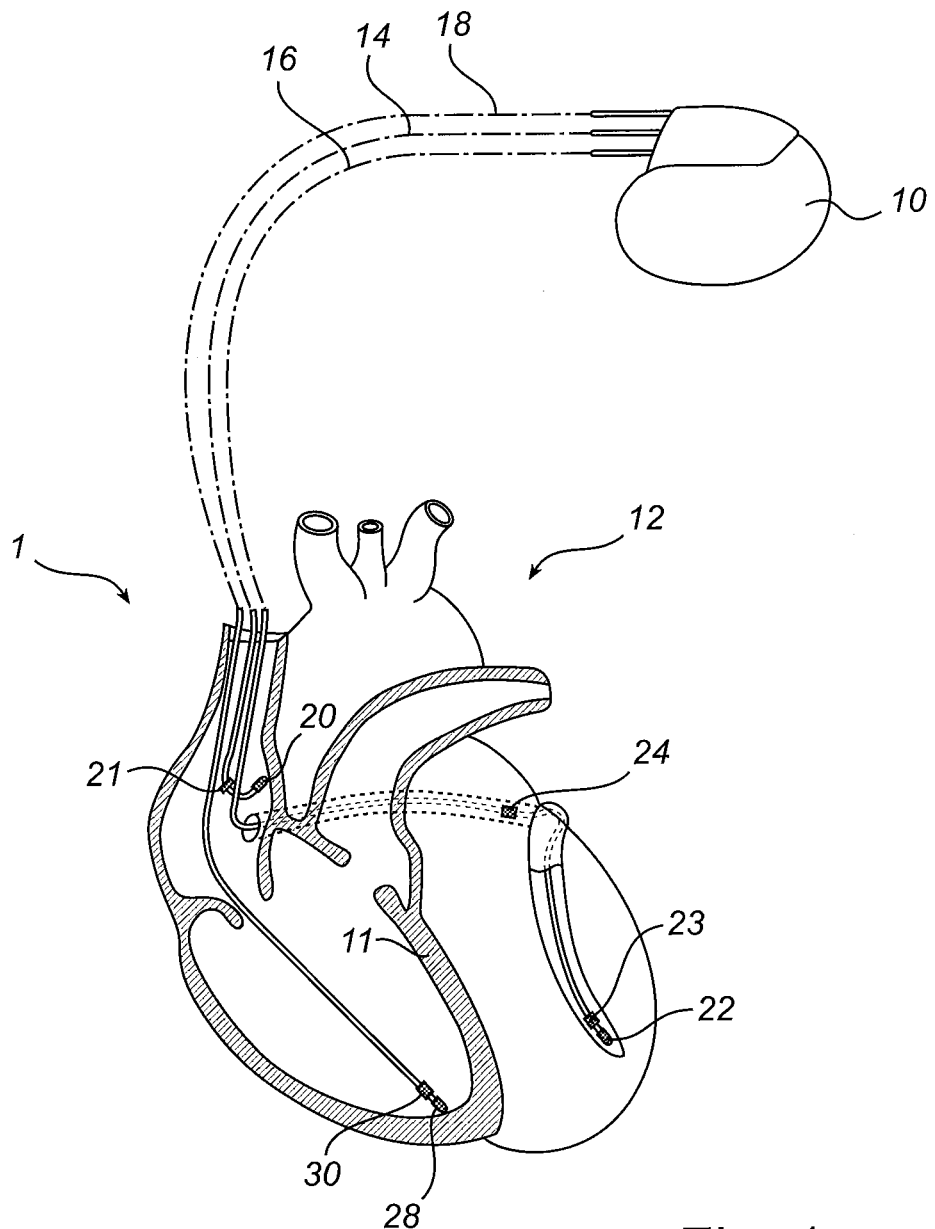
FIG. 1 is a simplified and schematic diagram of one embodiment of a system configuration according to the present invention including an implantable stimulation device in electrical communication with several leads implanted in a patient's heart for detecting cardiac activity and for delivering multi-chamber stimulation.

Referring to FIG. 1, one implementation of the present invention relating to a system including an implantable cardiac stimulator connectable to one or more medical leads will be discussed. FIG. 1 illustrates an implantable medical device (IMD), in the embodiments described below a cardiac stimulator 10, coupled to a heart 12. The implantable medical device may be a cardiac pacemaker, an implantable cardioverter defibrillator ("ICD"), a defibrillator, or an ICD coupled with a pacemaker implemented in accordance with embodiments of the present invention. The implantable medical device may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD may monitor cardiac signals and based thereof, identify potentially abnormal physiology (e.g. ischemia). The detected cardiac signals may include intrinsic heart beats that have no assistance from any type of manmade electrical stimulation. Alternatively, the detected cardiac signals may include heart beats that have been stimulated by an electrical source to produce a paced heartbeat. The electrical source that provides low energy electrical signals, such as provided by a pacemaker, a demand pacemaker, a single-chamber, a dual-chamber pacemaker, a biventricular pacemaker, and the like. Optionally, the paced heartbeat may be generated by an implantable device that provides high energy electrical signals such as those provided by an implantable cardioverter defibrillator.

The implantable cardiac stimulator 10 of the system 1 is in electrical communication with a patient's heart 12 by way of three leads 14, 16, and 18 suitable for delivering multichamber stimulation therapy.

To sense atrial signals and to provide right atrial chamber stimulation therapy, the stimulator 10 is coupled to an implantable right atrial lead 14 having, for example, an atrial tip electrode 20, which typically is implanted in the patient's right atrial appendage or septum. FIG. 1 shows the right atrial lead 14 as also having an atrial ring electrode 21.

To sense left atrial and ventricular cardiac signals and to provide left chamber pacing therapy the stimulator 10 is coupled to a coronary sinus lead 16 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

The lead 16 is designed to receive atrial and ventricular cardiac signals and to deliver left ventricular pacing therapy using, for example, a left ventricular tip electrode 22, a left ventricular ring electrode 23, and left atrial pacing therapy using, for example, a left atrial ring electrode 24.

The cardiac stimulator 10 is also in electrical communication with the heart 12 by way of an implantable right ventricular lead 18 having, in this embodiment, a right ventricular tip electrode 28 and a right ventricular ring electrode 30. Typically, the right ventricular lead 18 is transvenously inserted into the heart 12 to place the right ventricular tip electrode 28 in the right ventricular apex. The right ventricular lead 18 is capable of sensing or receiving cardiac signals, and delivering stimulation in the form of pacing therapy.

The cardiac stimulator 10 may be used to collect cardiac signals (e.g. both intrinsic and paced heart beats). Initially, the cardiac stimulator 10 may collect baseline cardiac signals and programmable controller (e.g. processor) 41 (shown in FIG. 2) may determine ST segment variations for the baseline signals. The baseline cardiac signals and ST segment variations may be stored in memory 49 (shown in FIG. 2). The cardiac stimulator 10 may be reprogrammed by a programmer 54 (shown in FIG. 2) to adapt, for example, cardiac pacing settings. Further, the cardiac stimulator 10 may obtain cardiac signals (e.g. IEGM) on a beat-by-beat basis and store each heart in the memory 49. In addition, associated with each heart beat, the cardiac stimulator 10 may store the time the heart beat occurred and the heart rate of the heart beat. The processor 41 may determine the ST segment variation associated with the heart beat and store the ST segment variation associated with the heart beat the ST segment value in memory 49 as will be described below.

Figure 2:
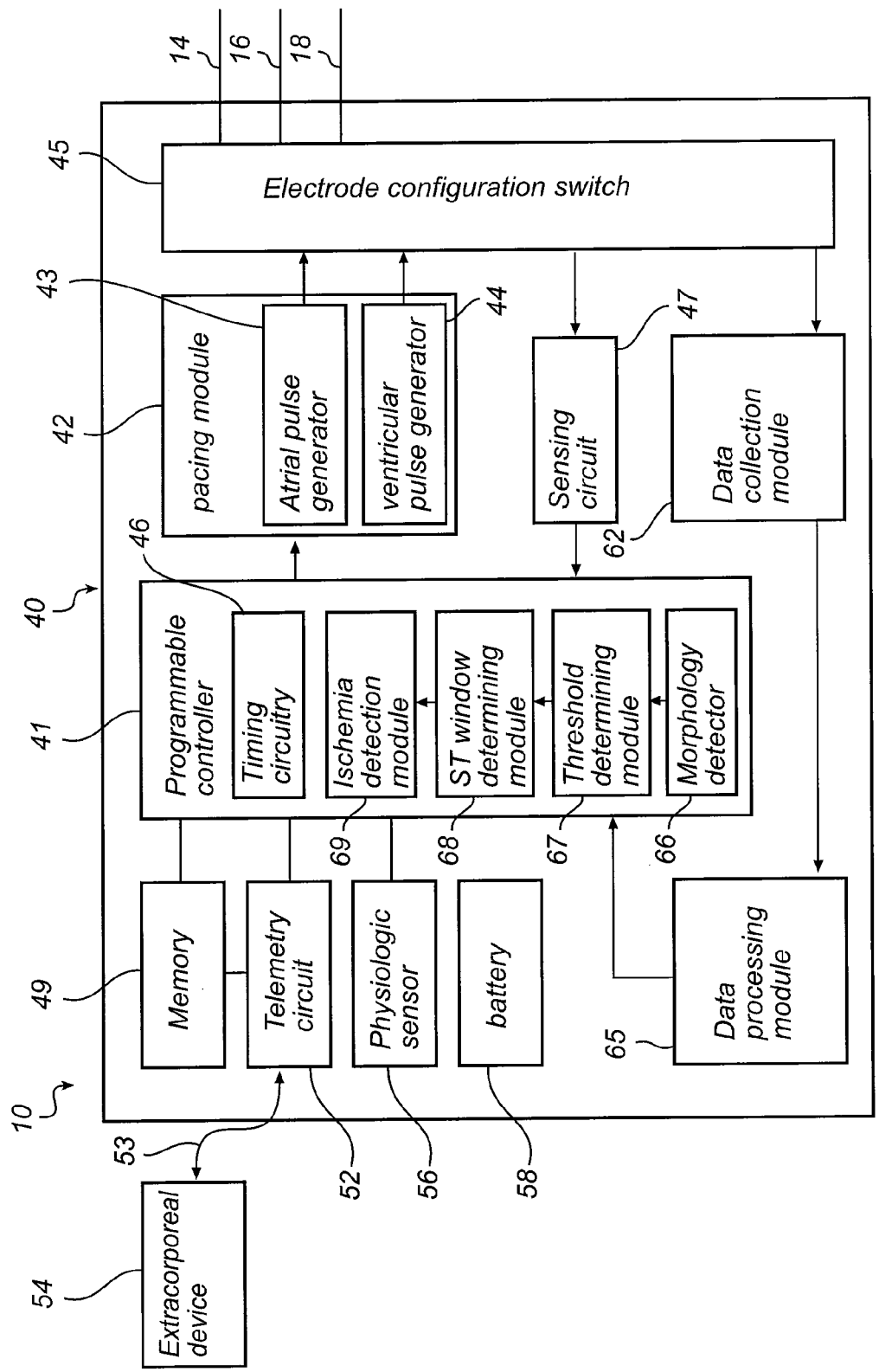
FIG. 2 is a simplified functional block diagram of one embodiment of a system in accordance with the present invention, illustrating basic elements of the system.

In FIG. 2, an exemplary, simplified block diagram depicting various components of the cardiac stimulator according to embodiments of the present invention is shown. The cardiac stimulator 10 is capable of delivering cardiac resynchronization therapy and is configured to integrate both monitoring and therapy features, as will be described below. Further, the cardiac stimulator 10 collects and processes data about the heart 12 from electrode pairs for sensing cardiac electrogram (EGM) signals. While a particular multi-chamber device is shown, it is to be appreciated and understood that this is done for illustration purposes only. Thus, the techniques and methods described below can be implemented in connection with any suitable configured or configurable stimulation device. Accordingly, one of skill in the art could readily duplicate, eliminate, or disable the appropriate circuitry in any desired combination to provide a device capable of treating the appropriate chamber with pacing stimulation including cardiac resynchronisation therapy.

The cardiac stimulator 10 has a housing 40, often referred to as the "can" or "case electrode". The housing 40 may function as a return electrode in "unipolar" modes. Further, the housing 40 includes connector (not shown) having a plurality of terminals (not shown) for connection with electrodes and/or sensors.

The cardiac stimulator 10 includes a programmable microcontroller or control module 41 that inter alia controls the various modes of stimulation therapy. As well known within the art, the microcontroller 41 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 41 includes the ability to process or monitor input signals (data or information) as controlled by a program stored in a designated block of memory. The type of microcontroller is not critical to the described implementations. Rather, any suitable microcontroller 41 may be used that carries out the functions described herein. The use of micro-processor based control circuits for performing timing and data analysis are well known in the art.

Furthermore, the cardiac stimulator 10 includes pacing module 42 adapted to provide pacing signals for delivery to the patient. The pacing module 42 comprises an atrial pulse generator 43 and a ventricular pulse generator 44 that generate pacing stimulation pulses for delivery by the right atrial lead 14, the coronary sinus lead 16, and/or the right ventricular lead 18 via an electrode configuration switch 45. It is understood that in order to provide stimulation therapy in each of the four chambers, the atrial and ventricular pulse generators 43 and 44, may include dedicated, independent pulse generators, multiplexed pulse generators, or shared pulse generators. The pulse generators 43 and 44 are controlled by the microcontroller 41 via appropriate control signals to trigger or inhibit stimulation pulses.

A data collection module 62 is adapted to collect, for example, cardiac signals such as IEGM signals. More specifically, the data collection module 62 is configured to collect IEGM signals, convert raw analog data into digital IEGM signals and store the digital IEGM signals in a memory for later processing or provide the digital IEGM signals to a data processing module 65 for pre-processing. Control signals from the microcontroller 41 determine when the data collection module 62 collects signals, stores them in the memory or transmit them to the data processing module 65. The data collection module 62 is coupled to the right atrial lead 14, the coronary sinus lead 16, and the right ventricular lead 18 to sample cardiac signals across any combination of electrodes.

The data processing module 65 is configured to pre-process the received digital IEGM signals including a filtering process. In one embodiment of the present invention, a $2^{nd}$ order Bessel filter with limiting frequencies 2 Hz and 20 Hz is used. Further, the signals may be filtered, reversed in the time domain, filtered again, and reversed in time again of the re-filtered signal. Thereby, the morphological changes induced by the filtering can be reduced and the time delays imposed by the filtering steps can be removed. A re-centering process may also be performed on the filtered signals including analyzing each heartbeat in a predetermined time window centered on an R-wave center, defined e.g. by the AnalyST™ algorithm provided by the applicant, where the greatest positive deflection is redefined as the heartbeat center. Moreover, the signals are differentiated with respect to time thus providing a derivative IEGM signal. The derivative IEGM signal is thereafter provided to the microcontroller 41.

The microcontroller 41 includes timing control circuitry 46 to control timing of the stimulation pulses (e.g. pacing rate, AV delay, VV delay, etc.) as well as to keep track of timing of refractory periods, blanking intervals, etc. which is well known in the art. In addition, the microcontroller 41 may include components such as e.g. an arrhythmia detector (not shown).

According to embodiments of the present invention, the microcontroller 41 comprises a morphology detector 66 configured to detect and identify cardiac events in IEGM signals and/or derivative IEGM signals. According to embodiments of the present invention, the morphology detector 66 detects and identifies the R-wave for each heartbeat or cardiac cycle in the derivative IEGM signal. The morphology detector can also operate on the original IEGM signal for identifying R-Waves.

Figure 3A:
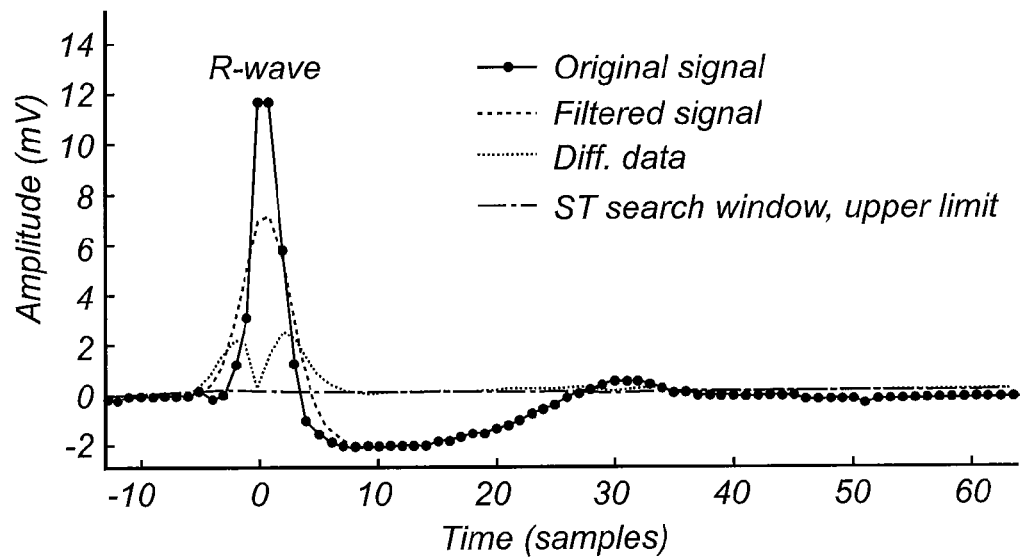
FIG. 3a is a diagram showing original IEGM signal, the pre-processed signal, the rectified derivative IEGM signal, and ST threshold (coinciding with the ST search window). The period starting at 7 and ending at 16 samples is found to be the ST window for this heartbeat.

In FIG. 3a, an original IEGM signal is shown together with the pre-processed signal (filtered) and the derivative signal. An ST search window is also shown. The R-wave is indicated in the diagram.

A threshold determining module 67 is configured to determine a threshold used for identifying the ST windows. According to an embodiment of the present invention, the threshold is determined as follows:

All samples in the window to be analyzed following the R-wave are extracted.

The $30^{th}$ percentile value among these samples is identified. This is a preferred value and can be adapted to, for example, a specific patient.

The $30^{th}$ percentile value is set as the threshold value.

The length of the search window is about 150-300 ms and preferably about 200-300 ms, a more preferably about 250-285 and starts at the R-wave of each cardiac cycle. In one specific embodiment, the search window is about 275 ms.

Figure 3B:
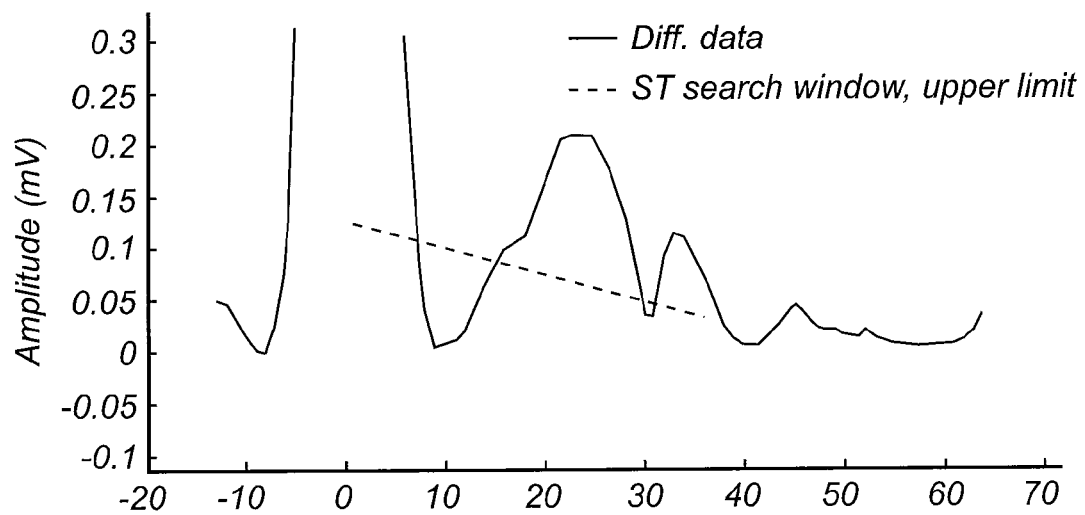
FIG. 3b is a diagram showing the rectified derivative IEGM signal and the threshold superimposed of FIG. 3a in more detail. The length of the threshold coincides with the ST search window. The period starting at 7 and ending at 16 samples is found to be the ST window for this heartbeat.

To reduce the risk of having a ST window that starts too far away from the R-wave and/or too close to the T-wave, the threshold may be set to a higher value in an area close to the R-wave. Thus, the threshold is set to be higher at the start and lower at the end. In a preferred embodiment of the present invention, the threshold is linearly decreasing from the starting point to the end point. In a preferred embodiment of the present invention, the start value is a first multiplying factor (e.g. 1.5, 2, 2.2 or 2.5) times the $30^{th}$ percentile value and the end value is a second multiplying factor (e.g. ¼, ⅓, ½ or ¼) of the $30^{th}$ percentile value. In FIG. 3b, the rectified derivative IEGM signal is shown together with a linearly decreasing threshold. The length of the threshold coincides with ST search window in this case. The period starting at 7 and ending at 16 samples is found to be the ST window for this heartbeat. However, other shapes of the decreasing threshold can also be used, e.g. quadric, exponential, logarithmic, stepwise etc.

Furthermore, an ST window determining module 68 is configured to analyze the derivative signal data following the identified R-wave so as to find portions of the derivative signal comprising samples having lower values than the predetermined threshold. The ST window determining module 68 is configured to determine a portion of the derivative signal including samples having lower values than the threshold to correspond to a ST window for that cardiac cycle if that portion fulfills predetermined requirements. According to at least one of the embodiments of the present invention, the following requirements are fulfilled:

i) The derivative of a sample is lower than the threshold.

ii) All samples matching i) are consecutive with the exception of a gap of a preset length (in a preferred embodiment a gap of 7.8 ms=1 sample at 128 Hz is tolerated)

iii) The portion of the derivative signal having such consecutive samples below the threshold is longer than a minimum allowed ST window. In a preferred embodiment, the minimum length is about 20-30 ms, and in more preferred embodiment the minimum length is about 25 ms.

When a predetermined number of ST windows have been determined, i.e. the ST start and duration has been determined for respective cardiac cycles, an overall ST start and duration are determined based on these ST windows. This can be performed when ST start and duration has been established for a large enough portion of the analyzed heart beats, for example, more than 50%, 60% or 65%. The overall ST window can be determined by calculating the median of starting points and durations. It is however also possible to calculate the average, the average of a percentile, a weighted average etc.

The ST window determining module 68 may further be configured to perform a verification procedure to verify parameters of the overall ST window, i.e. starting point, duration and end point. The starting point, duration and end point are therefore analyzed to verify that they are within allowed ranges. If not, the parameters can be adjusted to fit into the ranges, or they can be recalculated. By way of example, according to an embodiment of the present invention, the ranges are the following:

The minimum allowed ST start value from the R-wave, for example, from the peak value of the R-wave is between 15-80 ms, and is preferably between 20-60 ms, and more preferably between 20-30 ms. An example of a minimum ST start value is 24 ms from the R-wave, for example, from the peak value of the R-wave. Another example minimum start value is 40 ms from the R-wave, for example, from the peak value of the R-wave.

The maximum allowed ST start value from the R-wave, for example, from the peak value of the R-wave is between 50-300 ms, and preferably between 100-280 ms, and more preferably between 200-270 ms. An example of a maximum ST start value is 250 ms from the R-wave, for example, from the peak value of the R-wave. Another example of the maximum start value is 110 ms from the R-wave, for example, from the peak value of the R-wave.

The maximum ST end time from the R-wave, for example, from the peak value of the R-wave is between 200-300 ms, and preferably between 220-290 ms, and more preferably between 250-280 ms. An example of a maximum ST end time is 274 ms from the R-wave, for example, from the peak value of the R-wave.

A maximum duration value may also be applied, for example, between 30-90 ms, or preferably between 40-80 ms, or more preferably between 50-70 ms. In one specific embodiment, the maximum duration value is about 60 ms.

An ischemia detection module 69 is configured to use the overall ST window as a reference ST window in detecting ischemia by comparing IEGM data in the reference ST window with current IEGM data from a segment of the IEGM signal corresponding to the reference ST window. By comparing the reference ST window with current IEGM data in the corresponding window, shifts in the ST segment can be monitored, which are an indicator of a potential abnormal physiology, such as, ischemia.

The aforementioned components may be implemented as part of the microcontroller 41, or as software/firmware instructions programmed into the device and executed on the microcontroller 41 during certain modes of operation. Several of the components discussed above such as the threshold determining module 67, the ST determining module 68 and the ischemia detection module may be implemented in an extracorporal device such as a programmer. In fact there are several different possibilities to split components between the cardiac stimulator and the external instrument.

Moreover, the cardiac stimulator 10 additionally includes a battery 58 that provides operating power to all of the circuits shown in FIG. 2. Preferably, the stimulator 10 employs lithium or similar battery technology.

Figure 4:
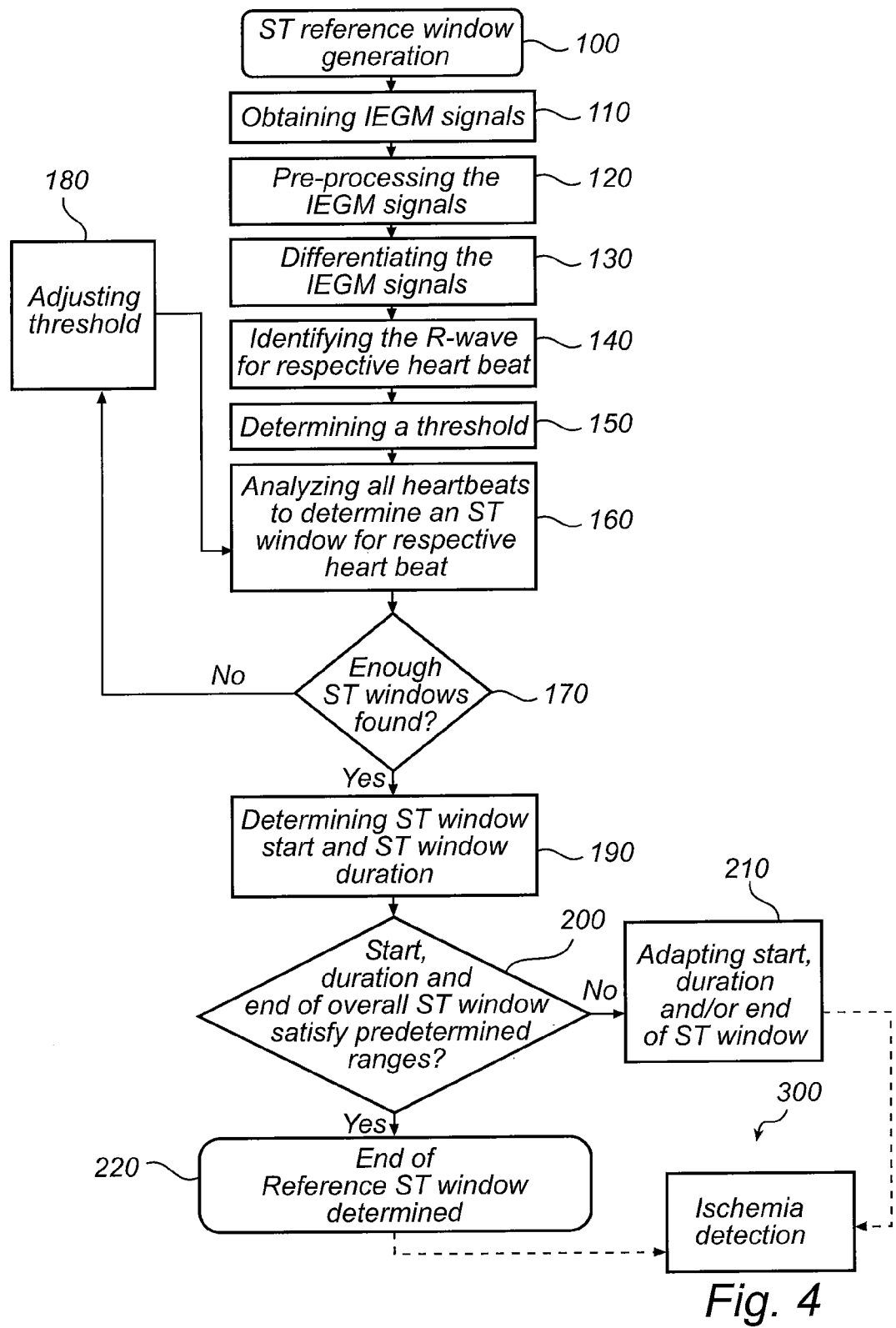
FIG. 4 is a flow diagram of an ST window determining process, which may be performed by a cardiac stimulator configured in accordance with example embodiments of the invention.

With reference now to FIG. 4, an embodiment of the method for generating a patient specific ST window according to the present invention will be discussed. FIG. 4 is a flow diagram of a ST window generation process 100, which may be performed by a cardiac stimulator configured in accordance with an example embodiment of the inventions, for example, as illustrated in FIG. 2. The various tasks performed in connection with the process 100 may be performed by software, hardware, firmware, or any combination thereof. For illustrative purposes, the following description of the process 100 refers to elements mentioned above in connection with FIGS. 1-2. In practical embodiments, portions of the process 100 may be performed by different elements of the described cardiac stimulator. It should be appreciated that the process 100 may include any number of additional or alternative tasks, the tasks shown in FIG. 4 need not be performed in the illustrated order, and the process 100 may be incorporated into a more comprehensive procedure or process having additional functionality not described in detail herein.

The process 100 obtains at least one IEGM signal indicating cardiac behavior of a cardiac cycle corresponding a heartbeat, in task 110, using the data collection module 62 which is configured to obtain data about the patient.

The IEGM signals are pre-processed in task 120 by the data processing module 65. For example, the signals may be re-centered and filtered, e.g. by using a $2^{nd}$ order Bessel filter with limiting frequencies 2 Hz and 20 Hz as have been described above.

In task 130, the IEGM signals are differentiated with respect to time in the data processing module 65.

Thereafter, in task 140, the R-wave is identified in the derivative signal for respective heart beat in the morphology detector 66. The R-wave can also be identified by analyzing the original IEGM-signal, for example through amplitude comparison with a predetermined value.

The threshold determining module 67 determines a threshold used for identifying the ST windows in task 150 as has been described above. To reduce the risk of having an ST window that starts too far away from the R-wave and/or too close to the T-wave, the threshold may be set to a higher value in an area close to the R-wave. Thus, the threshold is set to be higher at the start and lower at the end as has been described above.

In task 160, the differentiated IEGM signal for respective heart beat is analyzed by the ST window determining module 68. Preferably, a signal portion following the identified R-wave is analyzed so as to find portions of the signal that comprises samples having lower values than a predetermined threshold. In at least some embodiments, by way of example, a portion of the differentiated signal for a cardiac cycle including samples having lower values than the threshold is determined to correspond to an ST window for that cardiac cycle if that portion fulfills predetermined requirements, which according to an embodiment of the present invention are:

(i) The derivative of a sample is lower than the threshold,
(ii) All samples matching i) are consecutive with the exception of a gap of a predetermined length (in a preferred embodiment a gap of 7.8 ms=1 sample at 128 Hz is tolerated), and
(iii) The portion of the derivative signal having such consecutive samples below the threshold is longer than a minimum allowed ST window. In a preferred embodiment, the minimum length is about 20-30 ms, and in more preferred embodiment the minimum length is about 25 ms.

In query task 170, it is checked whether enough ST windows have been found in the analysis, for example, more than 50%, 60% or 65% of the heart beats. Hence, it is checked that the number of ST windows found in relation to the total number of heart beats is not too low. If the number of identified ST windows is too low, the process 100 proceeds to task 180 where the threshold is adjusted to a higher value, i.e. the threshold is increased. Then, task 160 is repeated but with the adjusted threshold. Preferably, the present threshold is multiplied with 2, which entails that the inclination of the threshold is preserved. Another alternative is to change the percentile value or any other parameter that controls the threshold, in such a case the process 100 is repeated from task 150 instead. However, if enough ST windows have been found, the process 100 continues to task 190 where an overall ST window start point and ST window duration are determined based on all identified ST windows. In a preferred embodiment, the median of all start points and durations are calculated while ignoring the heart beats for which a ST window could not be determined. It is however also possible to calculate, for example, the average of one or more percentiles, a weighted average.

When the overall ST window start point and ST window duration have been determined, a verification of the determined start point and duration is performed in task 200. The ST window start point, the ST window duration and ST window end point are analyzed to check whether they fall within allowed ranges. If the start point, duration and/or end point fall outside predetermined ranges (discussed above), an adjustment is performed in task 210. For example, if the ST window start value is smaller than the lowest allowed value, it is changed to this lowest allowed value. In an alternative embodiment, the process 100 returns to task 150 for a new calculation of ST windows before the adjustment in task 210 is performed. If the overall ST window is approved, i.e. the start value, duration and end value are within the predetermined ranges, the process is finished and the overall ST window is ready for use as a reference ST window in, for example, ischemia detection in an ischemia detection process 300.

Although certain embodiments and examples have been described herein, it will be understood by those skilled in the art that many aspects of the devices and methods shown and described in the present disclosure may be differently combined and/or modified to form still further embodiments. Alternative embodiments and/or uses of the devices and methods described above and obvious modifications and equivalents thereof are intended to be within the scope of the present disclosure. Thus, it is intended that the scope of the present invention should not be limited by the particular embodiments described above, but should be determined by a fair reading of the claims that follow.

The invention claimed is:

1. A method for ischemia detection comprising:
    obtaining at least one IEGM signal representative of cardiac behavior of a patient over a period of time;
    calculating a derivative signal of the IEGM signal;
    identifying a R-wave in the derivative signal or in the IEGM signal;
    analyzing said derivative signal data following said identified R-wave so as to find portions of said derivative signal comprising samples having lower values than a predetermined threshold;
    determining a portion of said derivative signal including samples having lower values than said threshold to correspond to a ST window for that cardiac cycle if that portion fulfills predetermined requirements;
    creating a reference ST window based on a number of said determined ST windows; and
    detecting ischemia by comparing IEGM data in said reference ST window with current IEGM data from a segment of the IEGM signal corresponding to the reference ST window.

2. The method according to claim 1, further comprising determining said threshold based on derivative signal data following said identified R-wave, such that the threshold has a higher value in a region following said R-wave.

3. The method according to claim 2, wherein the step of determining said threshold comprises finding a threshold base sample having a value that satisfies predetermined requirements.

4. The method according to claim 2, wherein said threshold has a value at a starting point of a search window being a multiple of said value of said threshold base sample and a value at an end point of said search window being lower than said value of said threshold base sample, wherein said threshold is linearly decreasing between the value of the starting point and said end point.

5. The method according to claim 1, wherein said predetermined requirements for determining a portion of the derivative signal to be a ST window comprises:
    a predetermined number of samples in said portion has a value below said predetermined threshold;
    a predetermined number of samples having values below said threshold are consecutive; and
    the portion has a length exceeding a predetermined time interval.

6. The method according to claim 5, wherein said predetermined requirements for determining a portion of the derivative signal to be a ST window further comprises, if more than one portion fulfill said predetermined requirements to correspond to a ST window for that cardiac cycle, selecting the portion being closest to the R-wave to correspond to the ST window for that cardiac cycle.

7. The method according to claim 1, wherein the step of creating a reference ST window comprises:
    identifying a predetermined number of ST windows;
    determining a starting point of the reference ST window based on starting points for said determined ST windows; and
    determining an end point of the reference ST window based on end points for said determined ST windows.

8. The method according to claim 7, wherein the step of creating a reference ST window further comprises:
    if a predetermined number of ST windows has not been identified during a predetermined period of time or from a predetermined number of cardiac cycles, adjusting said threshold to a higher value;
    analyzing said derivative signals data following said identified R-wave for each cardiac cycle so as to find portions of said derivative signal comprising samples having lower values than said adjusted threshold; and
    determining a portion of said derivative signal including samples having lower values than said threshold to correspond to a ST window for that cardiac cycle if that portion fulfills predetermined requirements.

9. A system for ischemia detection comprising:
    a data collection module configured to obtain at least one IEGM signal indicating cardiac behavior of a cardiac cycle corresponding a heartbeat;
    a data processing module configured to calculate a derivative signal of the IEGM signal;
    a detector configured to identify a R-wave in the derivative signal or in the IEGM signal
    an ST window determining module configured to:
        analyze said derivative signal data following said identified R-wave so as to find portions of said derivative signal comprising samples having lower values than a predetermined threshold;
        determine a portion of said derivative signal including samples having lower values than said threshold to correspond to a ST window for that cardiac cycle if that portion fulfills predetermined requirements; and
        create a reference ST window based on a number of said determined ST windows; and
    an ischemia detection module configured to detect ischemia by comparing IEGM data in said reference ST window with current IEGM data from a segment of the IEGM signal corresponding to the reference ST window.

10. The system according to claim 9, further comprising a threshold determining module configured to determine said threshold based on derivative signal data following said identified R-wave, said threshold having a higher value in a region following said R-wave.

11. The system according to claim 10, wherein said threshold determining module is further configured to find a threshold base sample having a value that satisfies predetermined requirements.

12. The system according to claim 10, wherein said threshold determining module is further configured to determine a value of a starting point of a search window to be a multiple of said value of said threshold base sample and a value at an end point of said search window to be lower than said value of said threshold base sample, wherein said threshold is linearly decreasing between the value of the starting point and said end point.

13. The system according to claim 9, wherein said ST window determining module is further configured to determine requirements for determining a portion of the derivative signal to be a ST window, wherein said requirements comprises:

a predetermined number of samples in said portion has a value below said predetermined threshold;

a predetermined number of samples having values below said threshold are consecutive; and the portion has a length exceeding a predetermined time interval.

14. The system according to claim 13, wherein said requirements for determining a portion of the derivative signal to be a ST window further comprises, if more than one portion fulfill said predetermined requirements to correspond to a ST window for that cardiac cycle, selecting the portion being closest to the R-wave to correspond to the ST window for that cardiac cycle.

15. The system according to claim 9, wherein said ST window determining module is further configured to:

identify a predetermined number of ST windows;

determine a starting point of the reference ST window based on starting points for said determined ST windows; and determine an end point of the reference ST window based on end points for said determined ST windows.

16. The system according to claim 15, wherein said threshold determining module is further configured to, if a predetermined number of ST windows has not been identified during a predetermined period of time or from of a predetermined number of cardiac cycles, adjust said threshold to a higher value; and wherein said ST window determining module is further configured to:

analyze said derivative signal data following said identified R-wave for each cardiac cycle so as to find portions of said derivative signal comprising samples having lower values than said adjusted threshold; and determine a portion of said derivative signal including samples having lower values than said threshold to correspond to a ST window for that cardiac cycle if that portion fulfills predetermined requirements.

* * * * *